United States Patent [19]

Jouffret

[11] 4,151,183
[45] Apr. 24, 1979

[54] PROCESS FOR THE PREPARATION OF TRIMETHYL-P-BENZOQUINONE

[75] Inventor: Michel Jouffret, Francheville-le-Bas, France

[73] Assignee: Rhone Poulenc, S.A., Paris, France

[21] Appl. No.: 517,251

[22] Filed: Oct. 23, 1974

[30] Foreign Application Priority Data

Oct. 25, 1973 [FR] France ............................... 73 38090

[51] Int. Cl.² .................... C07C 45/16; C07C 49/64
[52] U.S. Cl. ................................................. 260/396 R
[58] Field of Search ................................... 260/396 R

[56] References Cited

U.S. PATENT DOCUMENTS 3,658,852   4/1972   Schuster ........................ 260/396 R

OTHER PUBLICATIONS

Tomaja et al., J. Org. Chem., vol. 35, No. 6, 1970, pp. 2029-2030.

Primary Examiner—Vivian Garner
Attorney, Agent, or Firm—Cushman, Darby & Cushman

[57] ABSTRACT

Trimethyl-p-benzoquinone is produced in good yields quickly by oxidation of 2,3,6-trimethyl-phenol in the presence of a complex cobalt salt of the general formula:

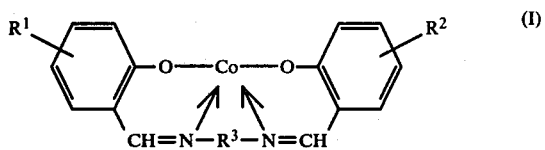

in which:

$R^1$ and $R^2$, which can be identical or different, each represents an alkoxy radical possessing 1 to 4 carbon atoms, and $R^3$ represents a divalent hydrocarbon radical possessing 2 to 15 carbon atoms, in an inert organic solvent medium.

9 Claims, No Drawings

PROCESS FOR THE PREPARATION OF TRIMETHYL-P-BENZOQUINONE

The present invention relates to a process for the preparation of trimethyl-p-benzoquinone by oxidation of 2,3,6-trimethyl-phenol.

Trimethyl-p-benzoquinone is the valuable starting material used to prepare trimethylhydroquinone which is the precursor of vitamin E. Various methods have been proposed for carrying out this oxidation. Amongst these, there may be mentioned the oxidation of 2,3,6-trimethyl-phenol by means of air or pure oxygen, in the presence of complex salts of cobalt and Schiff's bases derived from salicylaldehyde (see French patent application No. 2,015,576). The reaction is carried out in a carboxamide such as dimethylformamide. This process gives good yields, but requires long reaction times in order to obtain a high degree of conversion of trimethyl-phenol; its use consequently leads to a decrease in the productivity of the equipment. It is thus desirable to have available a process for the oxidation of 2,3,6-trimethyl-phenol to form trimethyl-p-benzoquinone, which makes it possible to overcome this disadvantage whilst retaining the advantages of the abovementioned process, in particular very good yields.

A process for the preparation of trimethyl-p-benzoquinone has now been found, according to the present invention, which consists of reacting 2,3,6-trimethyl-phenol with oxygen or with an oxygen-containing gas, in the presence of complex salts of cobalt and special Schiff's bases in an inert organic solvent medium, characterised in that the complex cobalt salts used are compounds of the general formula:

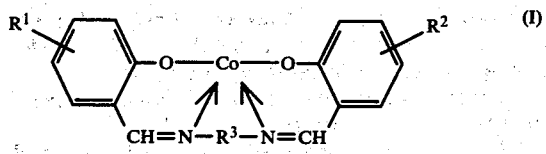

in which:
$R^1$ and $R^2$, which can be identical or different, each represents an alkoxy radical possessing 1 to 4 carbon atoms; and $R^3$ represents a divalent hydrocarbon radical possessing 2 to 15 carbon atoms.

Methoxy, ethoxy, propoxy, isopropoxy, butoxy and isobutoxy radicals may be mentioned as typical radicals $R^1$ and $R^2$. Alkylene radicals such as ethylene, propylene and butylene radicals, cycloalkylene radicals such as the cyclohexylene radical, and arylene radicals such as ortho- or meta-phenylene radicals may be mentioned as suitable divalent radicals $R^3$.

Specific examples of complex salts of cobalt and Schiff's bases, of the general formula (I), which are suitable include the salts prepared from the products resulting from the condensation: of diamines such as ethylene-diamine, 1,2-diamino-propane, 1,3-diamino-propane, 1,4-diamino-butane and ortho-phenylene-diamine, and hydroxy-alkoxy-carbonyl compounds such as 2-hydroxy-3-methoxy-benzaldehyde, 2-hydroxy-4-methoxy-benzaldehyde, 2-hydroxy-5-methoxy-benzaldehyde, 2-hydroxy-3-ethoxy-benzaldehyde, 2-hydroxy-4-ethoxy-benzaldehyde and 2-hydroxy-5-ethoxy-benzaldehyde.

The complex cobalt chelation compound prepared from the product resulting from the condensation of ethylene-diamine and 2-hydroxy-3-methoxy-benzaldehyde, and from the product resulting from the condensation of ethylene-diamine and 2-hydroxy-3-ethoxy-benzaldehyde, are particularly suitable.

The complex cobalt salts employed are known and can be prepared in accordance with the usual processes. For example, according to R. H. BAILES et al. J. Amer. Chem. Soc., 1947, 69, 1886, an aqueous solution of cobalt acetate is mixed with an alcoholic solution of the appropriate Schiff's base, at an elevated temperature, optionally in the presence of an alkaline base; the crystalline precipitate formed is filtered off, washed with water and then dried under a high vacuum.

The oxidation reaction takes place in the presence of an inert organic solvent which is liquid under the reaction conditions. Use can be made of aromatic hydrocarbons such as benzene, toluene or xylene, chlorinated aliphatic hydrocarbons such as chloroform, or lower aliphatic alcohols such as methanol, ethanol or propanol, but it is preferred to use aprotic polar solvents such as linear or cyclic caboxamides like dimethylformamide, diethylformamide or N-methylpyrrolidone, aliphatic or aromatic nitriles such as acetonitrile, propionitrile or benzonitrile, or organic sulphoxides such as, for example, dimethylsulphoxide. A preferred group of aprotic polar solvents are the aliphatic or aromatic nitriles; acetonitrile is particularly suitable.

It has been found, by comparison with the process described in the abovementioned French Patent Application, that the use of the complex cobalt salts of the formula (I) makes it possible considerably to increase the rate of reaction, to the extent of decreasing the time necessary for complete conversion of 2,3,6-trimethyl-phenol by more than half.

In practice, the process according to the invention can be carried out in the following way: trimethyl-phenol and the complex cobalt salt in the selected solvent are introduced into an oxidation apparatus, and then oxygen or an oxygen-containing gas is introduced under atmospheric or superatmospheric pressure. The mixture is then stirred at the desired temperature, until an amount of oxygen corresponding to the attachment of one molecule per molecule of trimethyl-phenol employed has disappeared. It is advantageous to work at temperatures from 0° to 60° C. preferably from 15° to 45° C.

The amount of complex cobalt salt used to carry out the reaction, expressed as the number of gram atoms of cobalt per mole of trimethyl-phenol, can vary within proportions, generally from 0.005 to 0.2; amounts from 0.02 to 0.08 are usually sufficient to effect the oxidation reaction rapidly.

The concentration of 2,3,6-trimethyl-phenol employed in the reaction medium is not critical and can vary within wide limits.

The treatment of the reaction medium to isolate the desired product from it can be carried out by any known method. It is possible, for example, to concentrate the reaction medium by distillation and then to filter off the solid product which has appeared, after washing the residue resulting from the concentration process with a suitable solvent, such as hexane or cyclohexane. The filtrate can then either be subjected to a fractional distillation in order to isolate from it trimethyl-p-benzoquinone in the pure state, or be treated directly by conventional techniques in order to form trimethyl-hydroquinone, the precursor of vitamin E.

The following Examples further illustrate the present invention. In these Examples: the complex cobalt salt prepared from the product resulting from the condensation of ethylene-diamine and 2-hydroxy-benzaldehyde is referred to as "salcomine," the complex cobalt salt prepared from the product resulting from the condensation of ethylene-diamine and 2-hydroxy-3-methoxy-benzaldehyde is referred to as "methoxysalcomine," and the complex cobalt salt prepared from the product resulting from the condensation of ethylene-diamine and 2-hydroxy-3-ethoxy-benzaldehyde is referred to as "ethoxysalcomine."

EXAMPLES 1 and 2

A 500 cc. glass flask, which is equipped with a blade stirrer and is connected to a supply of pure oxygen at atmospheric pressure, fitted out in such a way as to make it possible to read the volume of gas absorbed over a period of time, is employed.

Acetonitrile (158 cc.), 2,3,6-trimethyl-phenol (8.5 g; 0.0625 mol) and methoxysalcomine (1.0 g., corresponding to 0.0026 gram atom of cobalt) (Example 1) and ethoxysalcomine (1.08 g., corresponding to 0.0026 gram atom of cobalt) (Example 2) are introduced into this reactor.

The reactor is purged with oxygen and is then connected to the oxygen supply. Stirring is started, whilst keeping the temperature of the medium at 30° C. during the oxidation process. The reaction is stopped when the theoretical amount of oxygen has been consumed.

By way of comparison, these experiments were repeated using simple salcomine (0.845 g., corresponding to 0.0026 gram atom of cobalt) (Experiment A).

The yields of trimethyl-p-benzoquinone relative to the 2,3,6-trimethyl-phenol employed, are measured by vapor phase chromatographic analysis.

The following Table gives the results obtained:

TABLE

| Example/Experiment Complex Co Salt | 1 Methoxy-salcomine | 2 Ethoxy-salcomine | A Salcomine |
|---|---|---|---|
| Ratio: Co salt Trimethyl-phenol in gram atoms of Co/mol | 0.042 | 0.042 | 0.042 |
| Temperature, ° C. | 30° | 30° | 30° |
| Duration | 40 mins. | 20 mins. | 1 hr. 25 mins. |
| Degree of conversion of trimethyl-phenol | 100% | 100% | 100% |
| Yield of trimethyl-p-benzoquinone | 95% | 95% | 93% |

EXAMPLE 3

Dimethylformamide (158 cc.), 2,3,6-trimethyl-phenol (8.5 g.; 0.0625 mol) and ethoxysalcomine (1.08 g., corresponding to 0.0026 gram atom of cobalt) are introduced into a flask equipped as in Example 1.

The reaction is carried out as in Example 1, but without keeping the temperature at a particular value; it thus changes freely, during the oxidation process, from 25° C. to 44° C.

By way of comparison, the same experiment was repeated starting from simple salcomine (0.845 g., corresponding to 0.0026 gram atom of cobalt) (Experiment B).

The yields of trimethyl-p-benzoquinone relative to the 2,3,6-trimethyl-phenol employed, are measured by vapour phase chromatographic analysis.

The following Table gives the results obtained:

TABLE

| Example/Experiment Complex Co salt | 3 Ethoxysalcomine | B Salcomine |
|---|---|---|
| Ratio: Co salt Trimethyl-phenol in gram atoms of Co/mol | 0.042 | 0.042 |
| Temperature, ° C. | 25° to 44° | 25° to 40° |
| Duration | 40 mins. | 1 hr. 28 mins. |
| Degree of conversion of trimethyl-phenol | 100% | 100% |
| Yield of trimethyl-p-benzoquinone | 100% | 100% |

I claim:

1. In a process for the preparation of trimethyl-p-benzoquinone by reacting 2,3,6-trimethylphenol with oxygen or an oxygen-containing gas in the presence of a complex cobalt salt in an inert organic solvent, the improvement which comprises using, as the complex cobalt salt, a complex cobalt salt of the general formula:

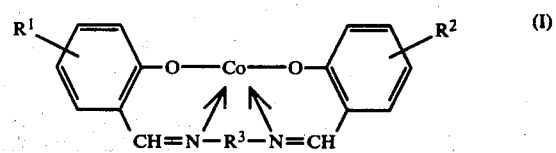

in which $R^1$ and $R^2$ each independently represents an alkoxy radical having 1–4 carbon atoms and $R^3$ represents an ethylene, propylene, butylene, cyclohexylene, ortho-phenylene or meta-phenylene radical.

2. Process according to claim 1, in which $R^1$ and $R^2$ are methoxy or ethoxy radicals.

3. Process according to claim 1, in which the complex cobalt salt is the complex of cobalt with either ethylene-diamine and 2-hydroxy-3-methoxy-benzaldehyde, or ethylene-diamine and 2-hydroxy-3-ethoxy-benzaldehyde.

4. Process according to claim 1, which is carried out at a temperature from 0° to 60° C. at atmospheric or superatmospheric pressure.

5. Process according to claim 1, in which the complex cobalt salt is used in an amount from 0.005 to 0.2 gram atom of cobalt per mol of trimethyl-phenol.

6. Process according to claim 5, in which the complex cobalt salt is used in an amount from 0.02 to 0.08 gram atom of cobalt per mol of trimethyl-phenol.

7. Process according to claim 1, which comprises reacting 2,3,6-trimethyl-phenol with oxygen or an oxygen-containing gas in the presence of a complex cobalt salt of the general formula (I) as defined in claim 1 in an aprotic polar solvent at 0° to 60° C., from 0.005 to 0.2 gram atom of cobalt being used per mol of trimethyl-phenol.

8. Process according to claim 1, wherein said solvent is selected from the group consisting of chlorinated aliphatic hydrocarbons, aromatic hydrocarbons, and lower aliphatic alcohols.

9. Process according to claim 1 in which the inert organic solvent is an aprotic polar solvent.

* * * * *